(12) United States Patent
Gao et al.

(10) Patent No.: US 10,600,629 B2
(45) Date of Patent: Mar. 24, 2020

(54) DETECTION OF ANALYTES USING POROUS MASS SPECTROMETRY SURFACE

(71) Applicant: The Regents of the University of California, Oakland, CA (US)

(72) Inventors: Jian Gao, Richmond, CA (US); Trent R. Northen, Walnut Creek, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/899,923

(22) Filed: Feb. 20, 2018

(65) Prior Publication Data

US 2018/0269052 A1 Sep. 20, 2018

Related U.S. Application Data

(60) Provisional application No. 62/472,932, filed on Mar. 17, 2017.

(51) Int. Cl.
| | |
|---|---|
| *H01J 49/40* | (2006.01) |
| *H01L 21/02* | (2006.01) |
| *H01J 49/16* | (2006.01) |
| *G01N 33/68* | (2006.01) |
| *H01J 49/04* | (2006.01) |

(52) U.S. Cl.
CPC ........ *H01J 49/164* (2013.01); *G01N 33/6848* (2013.01); *H01J 49/0418* (2013.01); *H01L 21/0203* (2013.01); *H01J 49/40* (2013.01)

(58) Field of Classification Search
CPC ........ H01J 49/04; H01J 49/00; H01J 49/0027; H01J 49/0031; H01J 49/036; H01J 49/025; H01J 49/0409; H01J 49/0413; H01J 49/0418; H01J 49/0422; H01J 49/0463; H01J 49/10; H01J 49/107; H01J 49/14; H01J 49/161; H01J 49/164; H01J 49/26; H01J 49/40; H01J 2237/2446; H01J 37/244; H01J 37/285; A61B 2576/02; A61B 5/14546; B01J 2219/00644; B01J 2219/00659; G01N 2560/00; H01L 21/0203

USPC ..... 250/281, 282, 288, 286, 287; 506/12, 32
See application file for complete search history.

(56) References Cited

U.S. PATENT DOCUMENTS

| | | | | |
|---|---|---|---|---|
| 8,575,544 | B1 * | 11/2013 | Kelly | H01J 37/244 |
| | | | | 250/281 |
| 8,704,167 | B2 * | 4/2014 | Cooks | C12Q 1/04 |
| | | | | 250/281 |
| 9,125,596 | B2 * | 9/2015 | Leclerc | A61B 5/1172 |
| 2008/0128608 | A1 * | 6/2008 | Northen | H01J 49/0413 |
| | | | | 250/282 |
| 2010/0056392 | A1 * | 3/2010 | Greving | G01N 33/6845 |
| | | | | 506/12 |
| 2018/0254177 | A1 * | 9/2018 | Gao | B82Y 40/00 |
| 2018/0269052 | A1 * | 9/2018 | Gao | H01J 49/164 |

* cited by examiner

*Primary Examiner* — David A Vanore
(74) *Attorney, Agent, or Firm* — Sheppard, Mullin, Richter & Hampton LLP

(57) ABSTRACT

The disclosure herein includes compositions and methods for ionizing targets and methods for making the compositions. In some embodiments, the compositions can include a porous substrate that has been etched for a desired average pore size, a desired porosity, or both for detection of one or more targets of interest. Also disclosed herein are methods for using the composition to ionize targets.

16 Claims, 9 Drawing Sheets

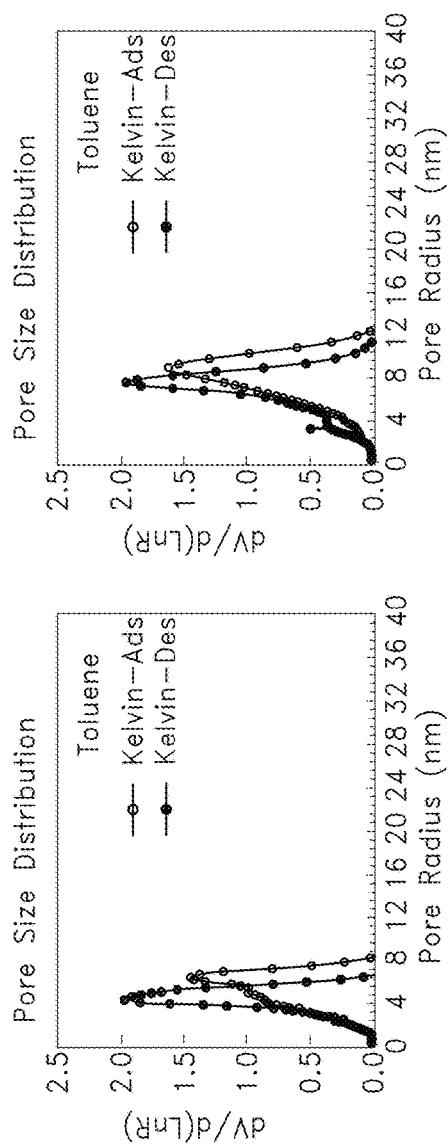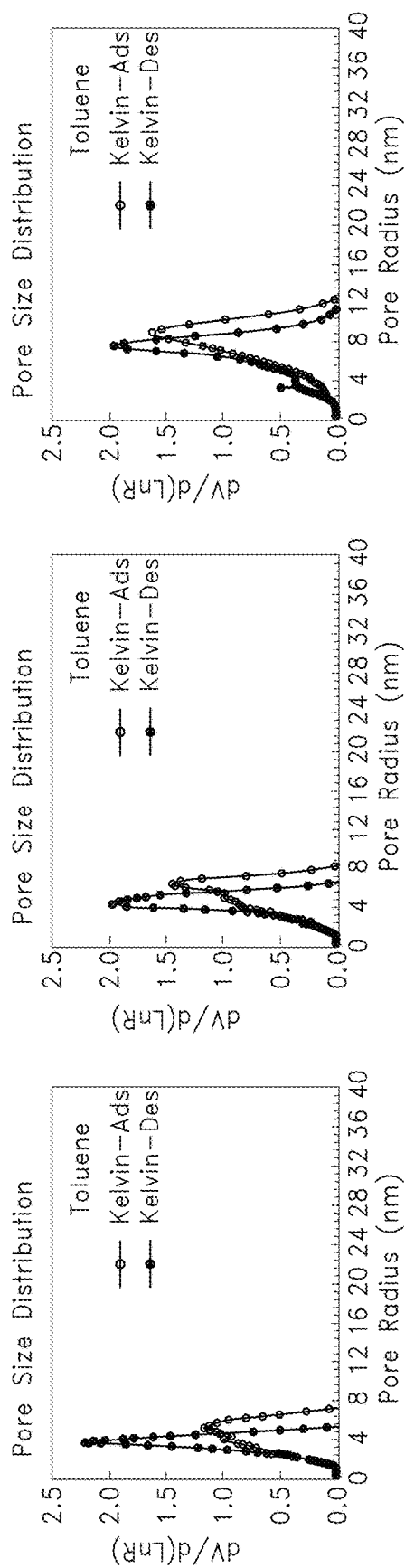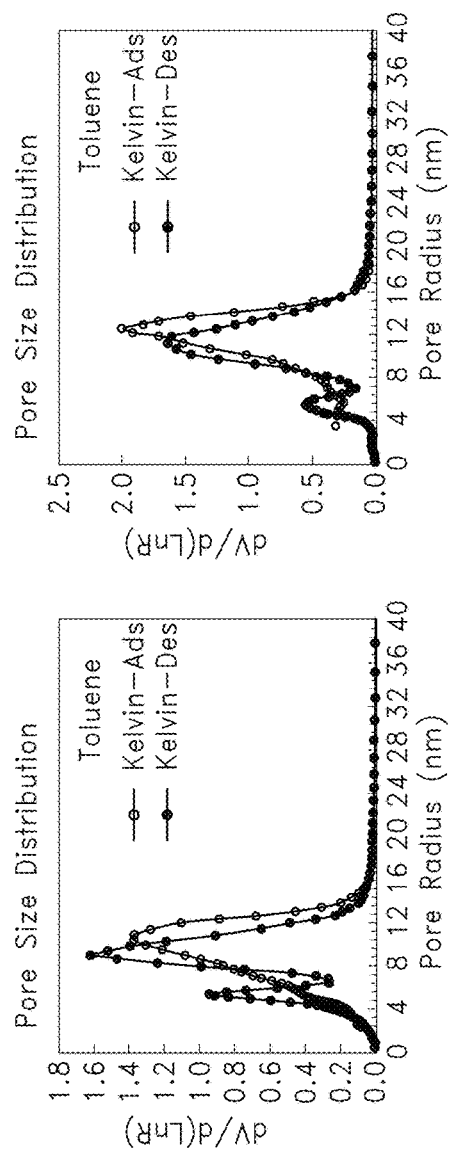
Figure.4A  Figure.4B  Figure.4C  Figure.4D  Figure.4E

DETECTION OF ANALYTES USING POROUS MASS SPECTROMETRY SURFACE

RELATED APPLICATIONS

This application claims the benefit of U.S. Provisional Application No. 62/472,932, filed Mar. 17, 2017. The content of the aforementioned application is expressly incorporated herein by reference in its entirety.

STATEMENT REGARDING FEDERALLY SPONSORED R&D

This invention was made with government support under Contract No. DE-SC0014079 awarded by the U.S. Department of Energy Office of Science, Contract No. AWD00000311 awarded by Defense Advanced Research Projects Agency (DARPA) Fold F(x) program, and Contract No. DE-AC02-05CH11231 awarded by the U.S. Department of Energy. The government has certain rights in the invention.

FIELD

The present application relates generally to the fields of biological and chemical analysis and detection. More specifically, the present application relates to compositions, methods and systems for analyzing and detecting analytes, for example biological or chemical molecules, as well as the methods suitable for making the composition and systems for analysis and detection.

BACKGROUND

There is a demand for extremely sensitive and non-destructive analytical techniques, for use in a wide variety of fields including biological and chemical assays. Mass spectrometry is one widely-used analytical method, which relies on ionization of a target molecule. Matrix-assisted laser desorption/ionization mass spectrometry (MALDI), which relies on a traditional preparation method, is limited by the necessity of co-crystallization of the analyte in a matrix. In addition, MALDI sensitivity, especially for low molecular weight analytes, is often limited by background noise due to ionization of matrix molecules. More recently-developed methods including DIOS have shown some success, but are limited in analyte scope. Nanostructure initiator mass spectrometry (NIMS) is a highly sensitive detection method, which has low background of direct analyzing a wide range of samples, such as biofluids, tissues and single cells. NIMS analysis uses a liquid initiator coated nanostructure surface that absorbs and transfers laser energy to analyte ions during the initiator vaporization phase. There is a need for designing mass spectrometry surfaces (e.g., NIMS surfaces) for increased metabolite detection sensitivity and coverage, and selective metabolite analysis.

SUMMARY

Provided herein includes a method for making a porous semiconductor substrate for ionizing a target. The method comprises, in some embodiments, (a) providing a semiconductor material; (b) determining a desired length of etching time of the semiconductor material based on the molecular weight of the target; (c) etching the semiconductor material for the desired length of etching time to produce an etched semiconductor material; and (d) contacting the etched semiconductor material with an initiator to produce the porous semiconductor substrate.

In some embodiments, in step (b) the desired length of etching time is determined to be no more than 20 minutes if the target is larger than 2000 Daltons in molecular weight. In some embodiments, in step (b) the desired length of etching time is determined to be about 1 minute to about 20 minutes if the target is larger than 2000 Daltons in molecular weight. In some embodiments, in step (b), the desired length of etching time is determined to be at least 15 minutes if the target is no more than 2000 Daltons in molecular weight. In some embodiments, in step (b), the desired length of etching time is determined to be at least 25 minutes if the target is no more than 2000 Daltons in molecular weight.

In some embodiments, step (b) comprises determining a desired porosity, a desired average pore size, or both of the porous semiconductor substrate based on the molecular weight of the target, wherein the desired length of etching time shows substantial positive linear correlation with the desired porosity, the desired pore size, or both of the porous semiconductor substrate. In some embodiments, in step (b) the desired porosity is determined to be no more than 40% if the target is larger than 2000 Daltons in molecular weight. In some embodiments, the desired porosity is determined to be no more than 35% if the target is larger than 2000 Daltons in molecular weight.

In some embodiments, in step (b) the desired porosity is determined to be at least 35% if the target is no more than 2000 Daltons in molecular weight. In some embodiments, in step (b) the desired porosity is determined to be at least 40% if the target is no more than 2000 Daltons in molecular weight. In some embodiments, in step (b) the desired average pore size is determined to be no more than 10 nm if the target is larger than 2000 Daltons in molecular weight. In some embodiments, in step (b) the desired average pore size is determined to be no more than 8 nm if the target is larger than 2000 Daltons in molecular weight. In some embodiments, in step (b) the desired average pore size is determined to be at least 8 nm if the target is no more than 2000 Daltons in molecular weight. In some embodiments, in step (b) the desired average pore size is determined to be about 10 nm to about 12 nm if the target is no more than 2000 Daltons in molecular weight.

In some embodiments, the semiconductor material is etched using hydrofluoric acid electrochemical etching method or inductively coupled plasma reactive ion etching method. In some embodiments, the semiconductor material is etched in the presence of hydrofluoric acid.

In some embodiments, the semiconductor material comprises a material selected from the group consisting of Group IV semiconductors, Group I-VII semiconductors, Group II-VI semiconductors, Group III-V semiconductors, sphaelerite structure semiconductors, Wurtzite Structure Compounds, I-II-VI2 semiconductors, silicon, and a combination thereof. In some embodiments, the semiconductor material comprises crystalline silicon. In some embodiments, the semiconductor material is a p-type silicon wafer.

In some embodiments, the initiator is a fluorinated molecule. In some embodiments, the initiator is selected from the group consisting of lauric acid, polysiloxanes, chlorosilanes, methoxy silanes, ethyoxy silanes, fluorous siloxanes and fluorous silanes. In some embodiments, the initiator is a polyfluorinated siloxane. In some embodiments, the initiator is bis(heptadecafluoro-1,1,2,2-tetrahydrodecyl)tetramethyldisiloxane.

In some embodiments, the target is selected from the group consisting of lipids, amino acids, small molecules, peptides, drugs, proteins, and any combination thereof.

Also disclosed herein includes a method for ionizing a target. The method, in some embodiments, comprises: providing a porous semiconductor substrate having a desired porosity, a desired average pore size, or both, wherein the desired porosity, the desired average pore size, or both are determined based on the molecular weight of the target; delivered the target to the semiconductor substrate to form a target-loaded substrate; and irradiating the target-loaded substrate.

In some embodiments, the method, further comprises (i) providing a semiconductor material; (ii) determining a desired length of etching time of the semiconductor material based on the molecular weight of the target, the desired porosity of the porous semiconductor substrate, the desired average pore size of the porous semiconductor substrate, or a combination thereof; (iii) etching the semiconductor material to produce an etched semiconductor material; and (iv) contacting the etched semiconductor material with an initiator to produce the porous semiconductor substrate having the desired porosity, the desired average pore size, or both.

In some embodiments, the desired porosity is no more than 40% if the target is larger than 2000 Daltons in molecular weight. In some embodiments, the desired porosity is no more than 35% if the target is larger than 2000 Daltons in molecular weight. In some embodiments, the desired porosity is at least 35% if the target is no more than 2000 Daltons in molecular weight. In some embodiments, in step (b) the desired porosity is at least 40% if the target is no more than 2000 Daltons in molecular weight. In some embodiments, the desired average pore size is no more than 10 nm if the target is larger than 2000 Daltons in molecular weight.

In some embodiments, the desired average pore size is no more than 8 nm if the target is larger than 2000 Daltons in molecular weight. In some embodiments, the desired average pore size is at least 8 nm if the target is no more than 2000 Daltons in molecular weight. In some embodiments, in step (b) the desired average pore size is determined to be about 10 nm to about 12 nm if the target is no more than 2000 Daltons in molecular weight.

In some embodiments, the semiconductor material comprises a material selected from the group consisting of Group IV semiconductors, Group I-VII semiconductors, Group II-VI semiconductors, Group III-V semiconductors, sphaelerite structure semiconductors, Wurtzite Structure Compounds, I-II-VI2 semiconductors, silicon, and a combination thereof. In some embodiments, the semiconductor material is a p-type semiconductor wafer. In some embodiments, the semiconductor material comprises crystalline silicon.

In some embodiments, the target is a constituent of a sample selected from a biological sample, an environmental sample, a clinical sample, a forensic sample, or a combination thereof. In some embodiments, irradiating the target-loaded substrate comprises irradiating the target-loaded substrate with a laser, an ion beam, or any combination thereof.

In some embodiments, delivering a target to the structured substrate comprises contacting a sample comprising the target to the substrate. In some embodiments, the sample is a biological sample, an environmental sample, a clinical sample, a forensic sample, or a combination thereof. In some embodiments, the sample comprises a tissue, a cell, a biofluid, or a combination thereof.

BRIEF DESCRIPTION OF THE DRAWINGS

FIG. 3A: 2 minutes; FIG. 3B: 10 minutes; FIG. 3C: 20 minutes; FIG. 3D: 30 minutes; and FIG. 4E: 40 minutes.

FIGS. 4A-4E are plots depicting pore size distributions of silicon surfaces obtained at various etching times. The etching times shown are as follows: FIG. 4A: 2 minutes; FIG. 4B: 10 minutes; FIG. 4C: 20 minutes; FIG. 4D: 30 minutes; and FIG. 4E: 40 minutes.

DETAILED DESCRIPTION

Figure 1:
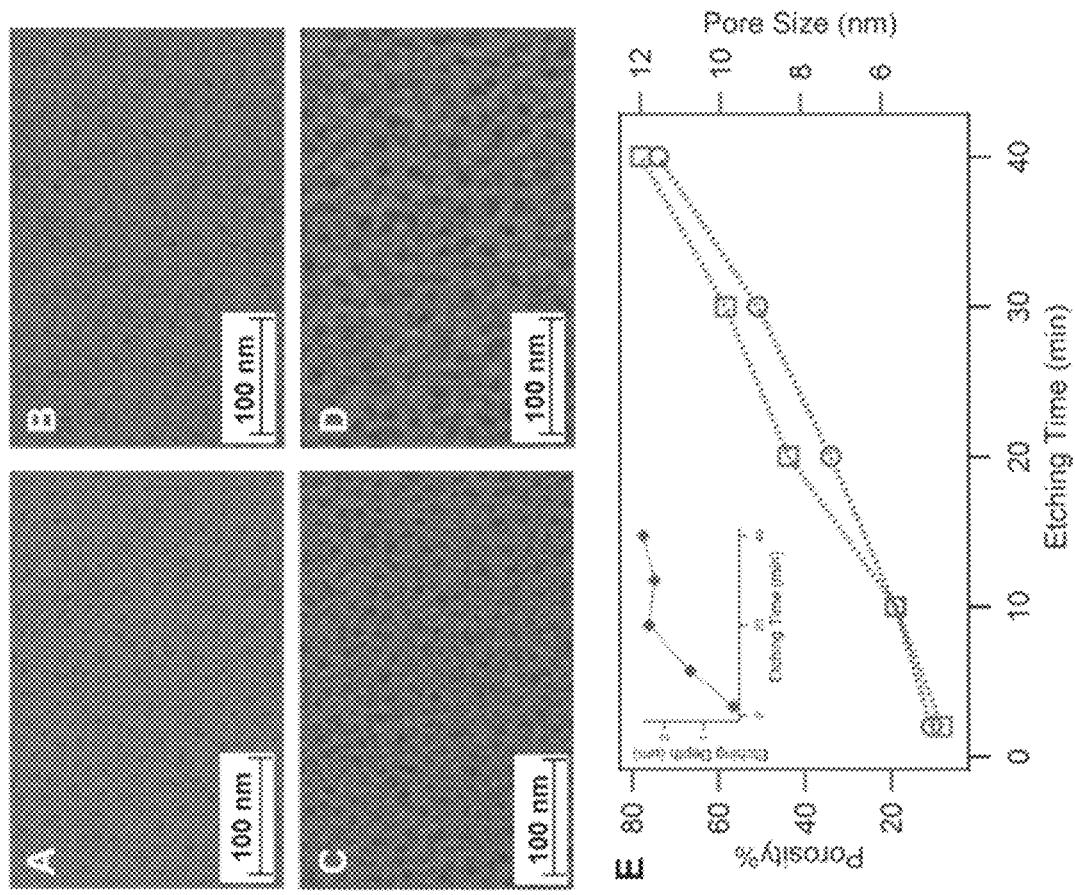
FIG. 1 shows SEM images of etched silicon surfaces obtained at variable etching durations. The etching times shown in the panels are as follows, Panel A: 2 mins; Panel B: 10 mins; Panel C: 25 mins; and Panel D: 40 mins. Panel E shows the correlations between surface morphologies of NIMS substrates and etching time with the line with circles representing porosity and the line with squares representing pore size. The inset graph on panel E shows the correlation between etched depth and etching time.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and made part of this disclosure.

Exemplary Mass spectrometry having porous surfaces prepared by HF electrochemical etching was described in U.S. Patent Publication No. 2008/0128608, which is incorporated by reference herein in the entirety.

The materials and methods provided herein are not limited to any particular theory or mode of operation. For instance, there are many possible explanations for surface morphology dependent ionization efficiency, such as variance according to melting point at the substrate surface, capillary action of the initiator along a surface, surface area, or laser absorption efficiency during a desorption/ionization process. The materials and methods provided herein are not intended to be construed to operate under a particular principle, but may be practiced by one of skill in the art according to technical knowledge and understanding at the time.

Definitions

Unless otherwise specifically noted herein, the terms set forth below will have the following definitions.

As used herein, the term "initiator" is used as understood by a person of skill in the art, and generally refers to a substance for promoting ionization of a target. Thus, an initiator is a substance other than the target and the substrate that improves ionization efficiency of a target. Generally the initiator is a fluid under the conditions chosen for ionization, for example a liquid. An initiator can have affinity for a structured surface as provided herein.

As used herein, the term "target" refers to any irradiation-ionizable molecule or compound.

Mass Spectrometry Surface Morphology

As disclosed herein, a structured substrate (e.g., a structured semiconductor substrate) can be a material that contains recesses (including but not limited to, openings, holes, void spaces, or a combination thereof). In some embodiments, the interior surfaces of the recesses can be modified with affinity coatings which can be bound to the substrate via covalent or non-covalent interactions. In some embodiments, these affinity coatings can be useful in localizing the initiator in the recesses of the substrate. Though not limited to the nanoscale, the structured substrates can preferably have nanoscale features. When the recesses have at least one nanoscale dimension, the substrate can be referred to as a "nanostructured substrate."

In some embodiments, the recesses in the structured substrates are pores. For example, pores can be spaces in the surface of a substrate having a transverse dimension parallel to the surface and a longitudinal dimension perpendicular to the surface. Pores can have a degree of irregularity to them making the specification of dimensions approximate. Pores in different materials can have different shapes also adding another degree of variability that requires some flexibility in the terminology of size and shape. Thus, while the term diameter can, and is, used with respect to pores, this is an approximate and average type of figure, and does not represent that pores have perfectly circular or regular cross-sections.

Disclosed herein includes a method for making a porous semiconductor substrate for ionizing a target of interest. As disclosed herein, but not bound by any particular theory, it is believed that adjusting etching time to make a porous semiconductor substrate (as a mass spectrometer surface) for detecting targets of interest can alter the porosity, the average pore size, or both of the resulting porous semiconductor substrate. The porosity, average pore size, or both of the porous semiconductor substrate can affect the sensitivity of the porous semiconductor substrate to targets with different molecular weights.

In some embodiments, the method comprises providing a semiconductor material; determining a desired length of etching time of the semiconductor material based on the molecular weight of the target of interest; etching the semiconductor material for the desired length of etching time to produce an etched semiconductor material; and contacting the etched semiconductor material with an initiator to produce the porous semiconductor substrate. In some embodiments, the porosity, the average pore size, or both of the substrates increases substantially linearly with the etching time. For example, the average pore size of the substrate can linearly increase from about 4 nm to about 12 nm when the etching time increases from about 0 minute to about 40 minutes. As another example, the porosity of the substrate can increase from about 7% to about 70% of the total etched volume when the etching time increases from about 0 minute to about 40 minutes. In the methods disclosed herein, the etching time can range, for example, from about 1 minute to about 40 minutes, based on the molecular weight of the target of interest. In some embodiments, wherein the target has a molecular weight of about 2000 Daltons or less, the etching time is 15 minutes or greater, for example 15, 16, 17, 18, 19, 20, 21, 22, 23, 24, 25, 26, 27, 28, 29, 30, 31, 32, 33, 34, 35, 36, 37, 38, 39, 40 minutes ("mins"), or a range between any of these two values. In some embodiments, if a target molecule has a molecular weight of about 2000 Daltons or less, the etching time is about 15 mins, about 20 mins, about 25 mins, about 30 mins, about 35 mins, about 40 mins, or any range in-between. In some embodiments, if the target has a molecular weight of about 2000 Daltons or more, the etching time is no more than 20 minutes, for example, 1, 2, 3, 4, 5, 6, 7, 8, 9, 10, 11, 12, 13, 14, 15, 16, 17, 18, 19, 20 minutes, or a range between any two of these values. In some embodiments, if the target has a molecular weight of about 2000 Daltons or more, the etching time is, or is about, 1 minute, 2 minutes, 3.5 minutes, 5 minutes, 10 minutes, 12 minutes, 14 minutes, or a range between any two of these values. As disclosed herein, the semiconductor material, the etched semiconductor material, the semiconductor substrate, or any combination can be doped or undoped.

The etched semiconductor material may be porous before being contacted with the initiator. In some embodiments, the method comprises providing a semiconductor material; determining a desired length of etching time of the semiconductor material based on the molecular weight of the target of interest; and etching the semiconductor material for the desired length of etching time to produce an etched semiconductor material that is porous. The average pore size of the etched semiconductor material can vary, for example from about 1 nm to about 50 nm. In some embodiments, the average pore size of the etched semiconductor material can be, or can be about, 1 nm, 2 nm, 3 nm, 5 nm, 10 nm, 15 nm, 20 nm, 25 nm, 30 nm, 35 nm, 40 nm, 45 nm, 50 nm, or more, or a range between any two of these values. In some embodiments, the average pore size of the etched semiconductor material can linearly increase with the etching time (e.g., the etching time from about 0 minute to about 40 minutes). The porosity of the etched semiconductor material can also vary, for example from about 5% to about 50% of the total etched volume.

In some embodiments, the pore size of a substrate corresponds with its porosity. In some embodiments, the pore size of a substrate does not correspond with its porosity. In some embodiments, the average pore size of the substrates be, or be about 1 nm, 2 nm, 3 nm, 4 nm, 5 nm, 6 nm, 7 nm, 8 nm, 9 nm, 10 nm, 11 nm, 12 nm, or a range between any two of these values. In some embodiments, the pore size is about 4 nm, about 4.5 nm, about 5 nm, about 5.5 nm, about 6 nm, about 6.5 nm, about 7 nm, about 7.5 nm, about 8 nm, about 8.5 nm, about 9 nm, about 9.5 nm, about 10 nm, about 10.5 nm, about 11 nm, about 11.5 nm, about 12 nm, or a range between any two of these values.

In some embodiments, the porosity of the substrate ranges from about 7% to about 70% of the total etched volume. In some embodiments, the porosity is about 20%, about 21%, about 22%, about 23%, about 24%, about 25%, about 26%, about 27%, about 28%, about 29%, about 30%, about 35%, about 40%, or any range in-between. In some embodiments, the porosity is about 30%, about 35%, about 40%, about 45%, about 50%, about 55%, about 60%, about 65%, about 70%, or a range between any two of these values.

The molecular weight of the targets can vary, for example, from 50 Dalton to about 10 kilo Daltons. In some embodiments, the molecular weight of the target is about 100 Dalton, 200 Dalton, 300 Dalton, 400 Dalton, 500 Dalton, 1000 Dalton, 2000 Dalton, 3000 Dalton, 4000 Dalton, 5000 Dalton, 6000 Dalton, or a range between any two of these values. In some embodiments, the target has a molecular weight of greater than about 2 kilo Daltons and the pore size of the substrate is less than 3 times the molecular size of the target molecule. In some embodiments, the target molecule has a molecular weight of greater than about 2 kilo Daltons and the pore size is about 2 times, about 1.75 times, about 1.5 times, about 1.25 times, about the same size as, about 0.75 times, about 0.5 times, about 0.25 times the molecular size of the target molecule, or any range in-between. In some embodiments, the target has a molecular weight of less than about 2 kilo Daltons and the pore size is greater than or equal to 3 times the molecular size of the target molecule. In some embodiments, the target molecule has a molecular weight of less than about 2 kilo Daltons and the pore size is about 3.25 times, about 3.5 times, about 3.75 times, about 4 times, about 4.25 times, about 4.5 times, about 4.75 times, about 5 times, about 5.25 times, about 5.5 times, about 5.75 times, about 6 times, about 6.25 times, about 6.5 times, about 6.75 times, about 7 times, about 7.25 times, about 7.5 times, about 7.75 times, or about 8 times the molecular size of the target molecule, or any range between any two of these values.

Substrate Materials

A variety of materials can be used to make porous semiconductor substrate. In some embodiments, a material is a semiconductor material. As provided herein, a semiconductor material can include, but not limited to, SiC, GaP, SixGex, Ge, and GaAs, and InP Group IV semiconductors (e.g., diamond), Group I-VII semiconductors (e.g., CuF, CuCl, CuBr, CuI, AgBr, and AgI), Group II-VI semiconductors (e.g., BeO, BeS, BeSe, BeTe, BePo, MgTe, ZnO, ZnS, ZnSe, ZnTe, ZnPo, CdS, CdSe, CdTe, CdPo, HgS, HgSe, and HgTe), Group III-V semiconductors (e.g., BN, BP, BAs, AlN, AlP, AlAs, AlSb, GaN, GaP, GaSb, InN, InAs, InSb), sphaelerite structure semiconductors (e.g., MnS, MnSe, (3-SiC, $Ga_2Te_3$, $In_2Te_3$, $MgGeP_2$, $ZnSnP_2$, and $ZnSnAs_2$), Wurtzite Structure Compounds (e.g., NaS, MnSe, SiC, MnTe, $Al_2S_3$, and $Al_2Se_3$), and I-II-VI2 semiconductors (e.g., $CuAlS_2$, $CuAlSe_2$, $CuAlTe_2$, $CuGaS_2$, $CuGaSe_2$, $CuGaTe_2$, $CuInS_2$, $CuInSe_2$, $CuInTe_2$, $CuTlS_2$, $CuTlSe_2$, $CuFeS_2$, $CuFeSe_2$, $CuLaS_2$, $AgAS_2$, $AgAlSe_2$, $AgAlTe_2$, $AgGaS_2$, $AgGaSe_2$, $AgGaTe_2$, $AgInS_2$, $AgInSe_2$, $AgInTe_2$, and $AgFeS_2$). Other conducting or semiconducting materials, such as metals and semimetals that are capable of transmitting energy to the initiator can also be used. In addition, other substrates, such as $Al_2O_3$, which are capable of absorbing radiation, may also be used in the composition, methods or systems disclosed herein when they absorb energy and transmit it to the initiator. In embodiments that use ion-beam irradiation, the material can be a non-light-absorbing material.

Many materials can be used as the substrate in the present invention. A preferred structured substrate is a nanostructured semiconductor substrate. More preferably, the structured substrate can be made of a semiconductor material that absorbs electromagnetic radiation (e.g., from a laser), such as porous silicon. In a preferred embodiment, a porous silicon substrate prepared from flat crystalline silicon can be used. Porous silicon surfaces can be strong absorbers of ultraviolet radiation. The preparation and photoluminescent nature of such porous silicon substrates has been described in Canham, *Appl. Phys. Lett.* 1990, 57, 1046; Cullis et al, *Appl. Phys. Lett.* 1997, 82, 909, 911-912; Siuzdak, et al., U.S. Pat. No. 6,288,390, which are incorporated by reference herein. The porous silicon substrate can be prepared using a simple galvanostatic etching procedure. See Cullis, *J. Appl. Phys.* 1997, 82, 909; Jung, et al *J. Electrochem. Soc.* 1993, 140, 3046; Properties of Porous Silicon (Canham ed., Institution of Electrical Engineers 1997), which are incorporated by reference herein. Undoped semiconductors can be prepared using light etching or simple chemical etching as is known to those skilled in the art. See, e.g., Jung, et al, *J. Electrochem. Soc.* 1993, 140, p. 3046-64. In a preferred method for creating a structured substrate, a p-type boron-doped silicon wafer can be etched using hydrofluoric acid (abbreviated as HF) in ethyl alcohol (abbreviated as EtOH or also called ethanol) solution. See Woo, H.-K.; Northen, T. R.; Yanes, O.; Siuzdak, G. *Nat. Protocols* 2008, 3, 1341-1349, which is incorporated by reference herein.

In some embodiments, the semiconductor is an extrinsic, or "doped" semiconductor. A doped semiconductor may be a n-type semiconductor. Generally, a n-type semiconductor includes one or more donor atoms. Non-limiting examples of donor atoms include phosphorous, arsenic, antimony, selenium, tellurium, and germanium. The doped semiconductor may be a p-type semiconductor. Generally, a p-type semiconductor includes one or more acceptor atoms. Non-limiting examples of acceptor atoms include boron, aluminum, gallium, beryllium, zinc, and cadmium.

Some materials provided herein may exhibit crystal planes, also referred to as a surface orientation. The crystal plane may be expressed by the Miller index, for example, as <001> or (111). Such crystal planes may affect surface properties of the substrate, and the method or methods best suited to modify the surface of the material. A person of skill in the art will be able to choose a suitable surface corresponding to the crystal plane, and a suitable method of modifying the surface. In some embodiments, the substrate is crystalline silicon having <100> orientation. However, a structured substrate provided herein is not intended to be limited to a particular crystal plane.

In some embodiments, the semiconductor material may be crystalline silicon. In some embodiments, the material selected may be silicon having p-type doping and <100> orientation. In still further embodiments, the silicon material may comprise a silicon wafer. The preparation of some silicon substrates has been described in, for example, Canham, *Appl. Phys. Lett.* 1990, 57, 1046; Cullis et al, *Appl. Phys. Lett.* 1997, 82, 909, 911-912; and Siuzdak, et al., U.S. Pat. No. 6,288,390, each of which is incorporated by reference herein in its entirety.

In some embodiments, the structured substrate can absorb electromagnetic radiation (for example, from a laser). In some embodiments a substrate, or a material having surface structures, can be a material that is compatible with ionization of a target by ion-beam irradiation.

Also disclosed herein are devices or systems (for example, spectrometers) comprising any of the etched surface materials disclosed herein. The type of the spectrometers can vary, for example, the spectrometer can be a mass spectrometer including but not limited to Matrix-assisted laser desorption/ionization mass spectrometry (MALDI) or Nanostructure initiator mass spectrometry (NIMS).

Initiators

Also provided herein are initiators useful for promoting ionization of a target. An initiator is a material other than the target that promotes or improves ionization efficiency or provides other benefit. Generally the initiator is a fluid, for example a liquid, which may be applied to a substrate (e.g., any of the substrate disclosed herein). Some initiator may remain in contact with the substrate after application to the substrate, even upon being blown with a jet of gas, for example, nitrogen. Furthermore, an initiator with affinity for a structured surface, as provided herein, should be chosen. In some embodiments, the initiator interacts with the substrate by non-covalent interactions. In some embodiments, an initiator is covalently or ionically bonded to a substrate. As provided herein, an initiator may be suited to a certain structured surface, to a class of structured surfaces, to a certain semiconductor material of substrate, or for ionization of a selected target.

An initiator that is transparent to UV light can be suitable for the methods, composition and system disclosed herein. In some preferred embodiments, the initiator does not ionize under the conditions used to ionize the target. Also preferably, the initiator does not covalently interact with target molecules.

Without intending to be limited by any particular theory, it is thought that the substrate absorbs energy upon irradiation and transfers the absorbed energy through the initiator to the target. The transfer of energy, it is thought, promotes desorption and ionization of the target.

In some embodiments, an initiator is a composition comprising, or is, a fluorinated molecule. In some embodiments, an initiator is a composition comprising, or is, a perfluorinated molecule. In some embodiments, the initiator is a composition comprising, or is, a polyfluorinated siloxane. In some embodiments, the initiator is a composition comprising, or is, a polyfluorinated silane. In some embodiments, the initiator is a composition comprising, or is, bis(heptadecafluoro-1,1,2,2-tetrahydrodecyl)tetramethyl di siloxane ("BisF17").

In some embodiments, the initiator is a composition comprising, or is, (heptadecafluoro-1,1,2,2-tetrahydrodecyl) dimethylchlorosilane, bis(tridecafluoro-1,1,2,2-tetrahydrooctyl)tetramethyldisiloxane; bis(tridecafluoro1,1,2,2tetrahydrooctyldimethylsiloxy)-methylchlorosilane, poly(3,3, 3-trifluoropropylmethylsiloxane), or any combination thereof. In some embodiments, the initiator is a composition comprising, or is chlorosilanes, chlorosiloxanes, or a combination thereof. In addition, structured substrates can also be treated with other kinds of aliphatic molecules, such as siloxanes, fatty acids, waxes, or a combination thereof. In some embodiments, the initiator is a composition comprising, or is, lauric acid, polysiloxanes, chlorosilanes, methoxy silanes, ethyoxy silanes, fluorous siloxanes, fluorous silanes, or a combination thereof. The initiator can be a single compound or a mixture of compounds.

In some embodiments, an initiator can comprise a compound:

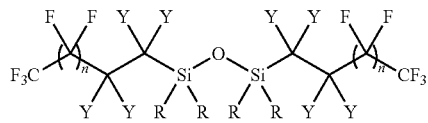

where each n is independently an integer between 4 and 20, an integer between 8 and 15, or an integer between 10 and 14; where each R is independently selected from $CH_3$, Cl, and $OCH_3$; and where each Y is independently selected from H and F.

In some embodiments, a target molecule is in contact with the initiator. In some embodiments, the target may interact weakly with the initiator such that the initiator and the target form separate phases. In some embodiments, an initiator in contact with a substrate is not in a crystalline form. In further embodiments, an initiator is not a crystal.

Targets

The targets suitable to be ionized by the compositions, methods and systems disclosed herein can vary. For example, the target may be of any class of ionizable molecules including, but not limited to, a small molecule, a metabolite, a biomolecule, a cell, a protein, a lysate, a lipid, an amino acid, a nucleic acid, a carbohydrate, a chemical compound, a peptide, a drug, or any combination thereof. Target molecules of any suitable mass may be chosen. In some embodiments, one target may be ionized. In further embodiments, more than one target may be ionized. In further embodiments, a target molecule can be selectively ionized. In still further embodiments, a selectively ionized molecule can be a small molecule, a metabolite, a biomolecule, a cell, a protein, a lysate, a lipid, an amino acid, a nucleic acid, a carbohydrate, a chemical compound, a peptide, a drug, or any combination thereof.

The target molecule can be a variety of molecular weights. In some embodiments, the target is a small molecule with a molecular weight of less than about 2 kilo Daltons. In some embodiments, the target is a molecule with a molecular weight of about 2 kilo Daltons or more.

In some embodiments, the target can be tagged, for example, fluorous tagged as described in, for example, Northen et al, "A nanostructure-initiator mass spectrometry-based enzyme activity assay" (2008), PNAS 105 (10) 3678-3683, which is incorporated by reference herein in the entirety.

In some embodiments, a target or targets, with or without accompanying additional materials, can be introduced to the substrate. A target can be present in a composition (e.g., a sample) with one or more additional components. Additional components can include, but are not limited to, buffers, metabolites, carriers, solvent, or any other suitable substance. The composition containing the target can be, for example, a biological sample, a clinical sample, an environmental sample, an industrial sample, a forensic sample, or a combination thereof. In some embodiments, the composition comprises a tissue, a cell, a biofluid, or a combination thereof. In some embodiments, a target present as a constituent of a biological sample can be ionized selectively. In further embodiments, a metabolite, a biomolecule, a cell, a protein, a lysate, a lipid, an amino acid, a nucleic acid, a carbohydrate, a chemical compound, a peptide, a drug, or any combination thereof present as a constituent of a biological sample can be ionized selectively.

Any application method that permits the target(s) to reach the surface of the substrate can be used. Such methods include delivery via an aliquot of solution, direct mechanical placement of solid target(s), and evaporation/condensation or sublimation/deposition of the target(s) onto the substrate. Such introduction can result in physical contact with the substrate, including adsorption or absorption. Introducing a target, by any means, to a substrate yields a "target-loaded substrate." For example, the target may be introduced in amounts of about 500 ymol to about 100 nmol of target, although appropriate quantities of target in a sample for a particular application will be apparent to one of skill in the art. A target being ionized to perform analysis (e.g. mass spectrometry) may be called an analyte. The materials and methods provided herein are compatible with a single target, or a plurality of targets in a single experiment. A plurality of targets may be present together in a sample mixture, or may be in distinct loci on the substrate, or may be a combination of these. In some embodiments, a target is not trapped in a crystal matrix.

Methods for Ionizing Targets

Also disclosed herein are methods of ionizing one or more targets, and methods of using the compositions for ionizing a target that are disclosed herein to detect and/or analyze one or more target analytes. In some embodiments, the method comprises providing a porous semiconductor substrate having a desired porosity, a desired average pore size, or both, wherein the desired porosity, the desired average pore size, or both are determined based on the molecular weight of the target; delivered the target to the semiconductor substrate to form a target-loaded substrate; and irradiating the target-loaded substrate. In some embodiments, the method further comprises providing a semiconductor material; determining a desired length of etching time of the semiconductor material based on the molecular weight of the target, the desired porosity of the porous semiconductor substrate, the desired average pore size of the porous semiconductor substrate, or a combination thereof; etching the semiconductor material to produce an etched semiconductor material; and contacting the etched semiconductor material with an initiator to produce the porous semiconductor substrate having the desired porosity, the desired average pore size, or both.

The substrate may be made of any suitable material as provided herein. In some embodiments, the substrate is a semiconductor substrate. In some embodiments, the substrate selected is a silicon substrate.

The substrate selected may be based on the particular application intended. The substrate may be selected to promote desorption or ionization of a target, to inhibit desorption or ionization of a molecule other than a target, or a combination of these. Although many combinations of target and substrate are possible, one of skill in the art will be able to select an appropriate substrate based on the guidance herein and on other knowledge available to such persons.

Any suitable method that results in contact between the initiator and the substrate may be used. For example, the initiator may be applied by soaking, dropping, dipping, spraying, printing, deposition, or condensation. In some embodiments, the initiator may be applied in combination with a carrier, for example a solvent. In such embodiments, the carrier may be removed by a suitable method such as blowing with gas or evaporation. In some embodiments, the initiator may be affixed to the substrate by a chemical reaction forming a covalent or ionic bond. In some embodiments, the interaction between the substrate and the initiator may be reversible. In general, a target can be applied to a substrate before, during, or after the time when an initiator is applied to the substrate.

A sample includes one or more targets. Any suitable method that results in contact between a target and the substrate may be used. For example, the sample may be applied by dropping, dipping, spraying, printing, deposition, or condensation. In some embodiments, the sample may be applied by an acoustic printer.

A suitable amount of target(s) deposited onto the substrate may vary, for example, from about 10 pmol to about 100 fmol, or from about 500 ymol to about 100 nmol, although other amounts may be appropriate depending on the application. In some embodiments, the amount of sample applied to the substrate should be chosen to provide the desired amount of a target.

In some embodiments, the target is applied in combination with other substances. The target may be applied concurrent with a carrier, for example, a solvent. The target may be adsorbed, dissolved, or suspended in the carrier. In some embodiments, the sample may be dissolved or suspended in a mixture of methanol and water. In some embodiments, the methanol:water ratio may be about 1:1 by volume to about 1:9 by volume. In some embodiments, formic acid may be added, for example, in about 0.01% to about 1% of solvent volume, about 0.05% to about 0.5%, or about 0.1% of solvent volume. In some embodiments, the carrier may be removed by a suitable method such as blowing or evaporation. A sample containing the target may be applied in any suitable amount, for example, about 1 nL, about 5 nL, about 10 nL, about 50 nL, or about 100 nL. The sample may also include additional substances such as buffers, sterilizing agents, stabilizing agents, and the like. In some embodiments, the sample may be an unpurified mixture from a biological source, for example, tissues, or blood or other fluid drawn from a subject.

In some embodiments, a plurality of samples may be applied to a substrate. In some embodiments, a single sample may be applied to a substrate in more than one locus. In some embodiments, a sample may be applied to the substrate such that loci on the substrate are correlated with loci in the sample. For example, a slice of a tissue may be applied to a substrate. In such embodiments, the irradiation of a certain locus on the substrate may ionize different targets, or different amounts of a target, than another locus on the same substrate.

In some embodiments, the prepared composition of substrate, initiator, and target(s) is irradiated. The irradiation may be by any suitable method. For example, the irradiation may be by laser or by ion beam.

In some embodiments, the laser source can be an ultraviolet pulse laser. In some embodiments, 50 to about 500 laser shots from a 337 nm pulsed nitrogen laser (Laser Science, Inc.) with a power of 2 to 50 µJ/pulse can be used. Irradiation can be done with a lens, and with an optional neutral density filter; these and other methods of focusing and filtering laser radiation being known to those skilled in the art. A preferred ion beam can be composed of positively charged clustered ions. In some embodiments, a cluster source, such as $Bi^{3+}$ ion source, can be used. Alternatively, other monoatomic and clustered ions can be used such as $Au^+$, $Ga^+$, and $Bi^+$.

The irradiation may be at any appropriate intensity and duration to promote desorption and ionization of a target. Generally, the intensity of irradiation should be selected so as to lead to substrate surface reorganization. In some embodiments, a single laser pulse or ion beam pulse may be used. In some embodiments, more than one laser pulses or ion beam pulses may be used. Although many variations are possible, one of skill in the art will be able to select an appropriate irradiation method based on the guidance herein and on other knowledge available to such persons.

The pressure during target desorption can vary substantially depending on the sensitivity desired. In some embodiments, the pressure is a pressure at which MALDI-MS can operate. In some embodiments, the pressure is a pressure at which atmospheric MALDI (AP-MALDI) is typically performed. In some embodiments, lower pressures can be used to improve sensitivity and lessen interference problems. In some embodiments, the pressure can be $10^{-6}$ to $10^{-7}$ torr. In some embodiments, higher reduced pressures can be used, up to atmospheric pressure.

In some embodiments, the mass-to-charge ratio of the ionized target may be determined. A variety of apparatuses may be used to measure the mass-to-charge ratio of the ionized target. In some embodiments, a time-of-flight mass analyzer may be used for detecting the desorbed and ionized target. When employed in the methods provided herein, the time-of-flight mass analyzer may be preceded by an ion reflector to correct for kinetic energy differences among ions of the same mass. In some embodiments, a brief delay between the desorption-ionization of the target and the application of the initial accelerating voltage by the mass analyzer may be allowed. In some embodiments, other mass analyzers, including magnetic ion cyclotron resonance instruments, deflection instruments, quadrupole mass analyzers, or other instruments known to one skilled in the art may be used.

In some embodiments, a commercial mass spectrometry system may be used, for example, an AB Sciex TOF/TOF 5800 MALDI mass spectrometry system. In some embodiments, positive ionization mode may be used. In some embodiments, negative ionization mode may be used. Post-collection processing may be employed, for example, MALDI MSI 4800 imaging software.

In some embodiments, a sample or samples may be applied to the substrate in more than one locus. In some embodiments, the locus or loci of a sample as applied to a substrate may be detected. In some embodiments, the irradiation may be focused at a particular area of the substrate, leading to ionization of a target or targets in a particular area of the substrate. One of skill in the art will appreciate that such localized ionization may be useful in determining the locus of a target, and thus a sample or part of a sample, on the substrate. In some embodiments, the location of a target can be correlated with its location in a sample, for example, a tissue, a forensic sample, an industrial sample, or an environmental sample.

It will be appreciated by one of skill in the art that the order in which the initiator is applied and the sample is delivered is not particularly limited. These steps may occur concurrently or sequentially, and any order is within the scope of the present disclosure. In some embodiments, the initiator may be applied before the sample is delivered. In some embodiments, the sample may be delivered before the initiator is applied.

EXAMPLES

Some aspects of the embodiments discussed above are disclosed in further detail in the following examples, which are not in any way intended to limit the scope of the present disclosure.

Example 1

Preparation of Substrate

Fabrication of Substrates.

This example illustrates a non-limiting process whereby a substrate can be prepared in a manner suitable to allow ionization by irradiation. Silicon wafers (4" diameter, 525 μm thickness, p-type with resistivity of 0.01-0.02 ohm/cm, backside oxide seal removed, purchased from Addison Engineering) were trimmed into 7.0 cm squares, and then cleaned in 3 solvent baths: trichloroethylene, acetone, and methanol for 15 minutes sequentially. The cleaned wafers were placed in a custom Teflon etching chamber with HF etching bath (24% HF, 26% water, 50% ethanol) and electrochemically etched at 2.36 A with etching times of 2, 3.5, 5, 10, 15, 20, 25, 30, 35, and 40 min, in duplicates. The etched wafers were soaked with the initiator BisF17 (purchased from Gelest) for 1 hour and used as NIMS substrates after removing the extra initiator with a nitrogen gun. The procedure for the fabrication of the substrates is stated in more detail within Woo, H.-K.; Northen, T. R.; Yanes, O.; Siuzdak, G. Nat. Protocols 2008, 3, 1341-1349, which is incorporated by reference herein in the entirety.

Materials.

Arginine (m/z 175.12+/−0.01 Da), palmitoylcarnitine (m/z 400.34+/−0.01 Da), streptomycin (m/z 582.27+/−0.01 Da), and insulin chain B oxidized (insulin B, m/z 3496.62+/−0.01 Da) were purchased from Sigma-Aldrich (St. Louis, Mo.). Bradykinin (m/z 904.47+/−0.01 Da), angiotensin (m/z 1296.68+/−0.01 Da), neurotensin (m/z 1672.92+/−0.01 Da), ACTH (clip 1-17) (m/z 2093.09+/−0.01 Da), ACTH (clip 18-39) (m/z 2465.20+/−0.01 Da) and ACTH (clip 7-38) (m/z 3657.92+/−0.01 Da) were purchased from AnaSpec (Fremont, Calif.) as a pre-mixed peptide mass standard kit. The compounds were each dissolved in a 1:1 methanol (J. T. Baker, LC-MS grade) to water (J. T. Baker, LC-MS grade) solution with 0.1% formic acid added (Sigma-Aldrich, MS grade) to reach a concentration of 10 mg/L. All the chemicals were of high purity grade, and were not further purified. Mass concentrations, common in mass spectrometry, were used in this study, Table 1 is provided below to enable comparison of molar concentrations.

TABLE 1

The corresponding molarities of the metabolites at 10 mg/L mass concentration.

| Metabolites | Concentration (μM) |
|---|---|
| Arginine | 57.5 |
| Palmitoylcarnitine | 25.1 |
| Streptomycin | 17.2 |
| Bradykinin | 11.1 |
| Angiotensin | 7.7 |
| Neurotensin | 6.0 |
| ACTH (clip 1-17) | 4.8 |
| ACTH (clip 18-39) | 4.1 |
| ACTH (clip 7-38) | 2.7 |
| Insulin B | 2.9 |

Surface Analysis.

A Zeiss Ultra 60-SEM (Oberkochen, Germany) was used to visualize the surface morphologies of these NIMS substrates, and the spectroscopic ellipsometer (Semilab SOPRA EPS, North Billerica, Mass.) was used to measure the optical properties of etched porous surfaces. The procedure for measuring the optical properties of etched porous surfaces is stated in more detail within each of which is incorporated by reference. Pore size and porosity of these surfaces were calculated using Winelli II software with Forouhi-Bloomer model. Analytes were transferred onto NIMS substrates using an acoustic printer (EDC ATS-100) and 10 nl of each analyte solution was deposited on the surfaces. An AB Sciex (Foster City, Calif.) TOF/TOF 5800 MALDI mass spectrometer configured at positive ionization mode was used for NIMS imaging of sample spot arrays, and the acquired data was converted and plotted with OpenMSI program.

Example 2

Electrochemical Etching to Control Surface Morphology

This example illustrates a non-limiting procedure whereby the surface morphology of the semiconductor substrate can be varied by various electrochemical etching methods. An anodic electrochemical etching method was chosen. Varying etching duration provided substrates with varying degrees of porosity.

Effect of Electrochemical Etching Time on Surface Morphology.

The anodic electrochemical etching method was used to create nanostructured features on monocrystalline silicon surface in HF bath. The anodic electrochemical etching method is described in more detail in Korotcenkov, G. *Porous Silicon: From Formation to Application: Formation and Properties, Volume One: Formation and Properties*; CRC Press, 2016, which is incorporated by reference herein in the entirety.

Figure 2:
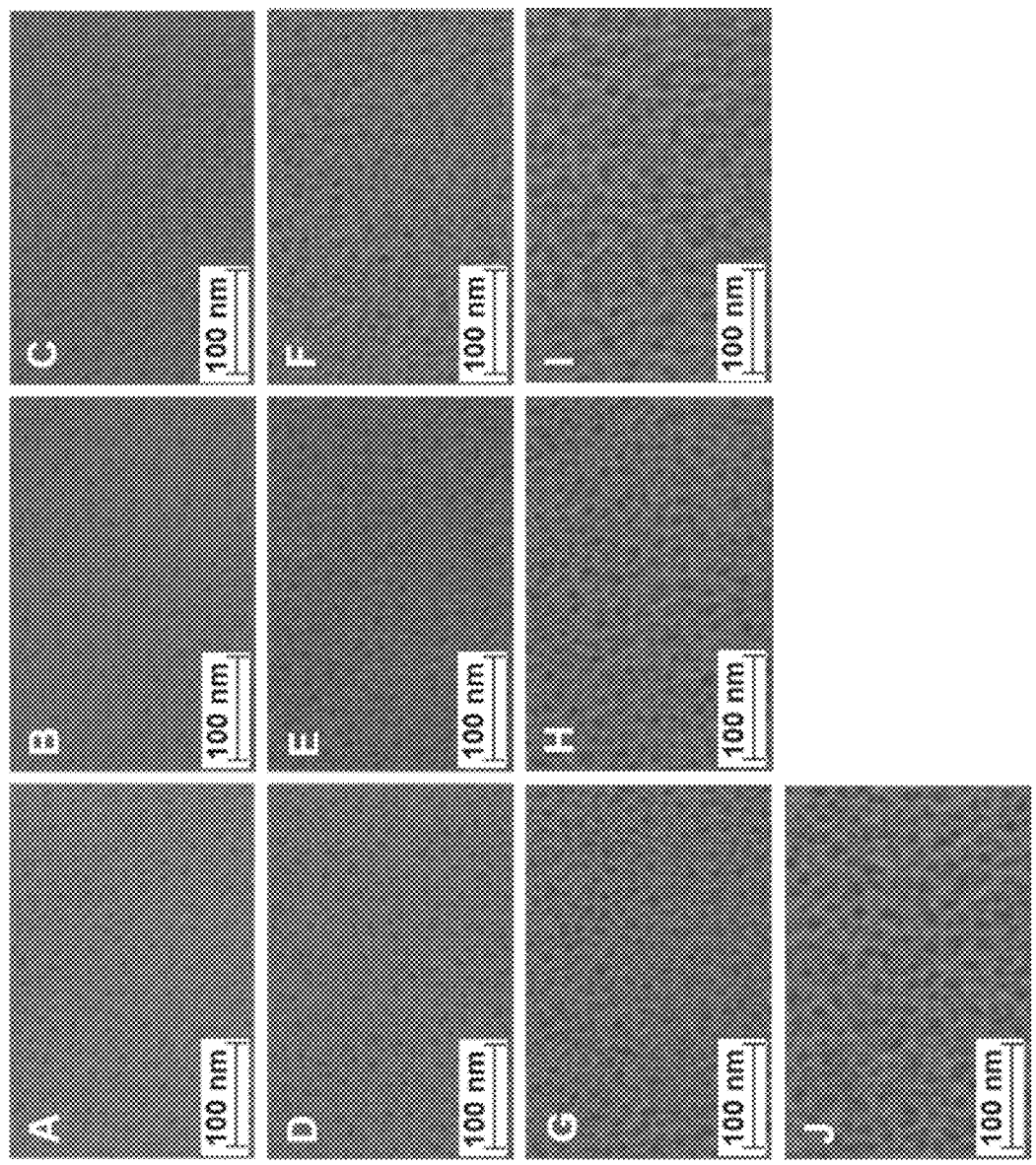
FIG. 2 depicts SEM images of silicon surfaces obtained at variable etching times. The etching time shown in the panels are as follows, Panel A: 2 mins; Panel B: 3.5 mins; Panel C: 5 mins; Panel D: 10 mins; Panel E: 15 mins; Panel F: 20 mins; Panel G: 25 mins; Panel H: 30 mins; Panel I: 35 mins; and Panel J: 40 mins.

The rate of pore formation was kept constant by fixing HF concentration, electric current density and silicon wafer properties. As shown in FIG. 1 panel E, the duration of the etching process was varied from 2 mins to 40 mins to adjust the surface morphologies of the substrates. FIG. 1 also shows the SEM images of silicon substrates with varying etching times: panel A: 2 mins; panel B: 10 mins; panel C: 25 mins; panel D: 40 mins. The SEM images show that porous structures are distributed homogeneously over entire etched surfaces, and that the pore size gradually increases with etching time. These porous nanostructures enable large surface area as well as low melting points that allow to efficiently convert analyte molecules into gas phase ions under low intensity laser irradiation. See Northen, T. R.; Woo, H.-K.; Northen, M. T.; Nordstrom, A.; Uritboonthail, W.; Turner, K. L.; Siuzdak, G. *Journal of the American Society for Mass Spectrometry* 2007, 18, 1945-1949, Gao, J.; de Raad, M.; Bowen, B. P.; Zuckermann, R. N.; Northen, T. R. *Analytical Chemistry* 2016, 88, 1625-1630, Stolee, J. A.; Walker, B. N.; Zorba, V.; Russo, R. E.; Vertes, A. *Physical Chemistry Chemical Physics* 2012, 14, 8453-8471, and Korotcenkov, G. *Porous Silicon: From Formation to Application: Biomedical and Sensor Applications, Volume Two: Biomedical and Sensor Applications*; CRC Press, 2016, which are incorporated by reference herein in the entirety. FIG. 2 shows further SEM images of silicon substrates with varying etching times: panel A: 2 mins, panel B: 3.5 mins, panel C: 5 mins, panel D: 10 mins, panel E: 15 mins, panel F: 20 mins, panel G: 25 mins, panel H: 30 mins, panel I: 35 mins, and panel J: 40 mins.

Figure 3A:
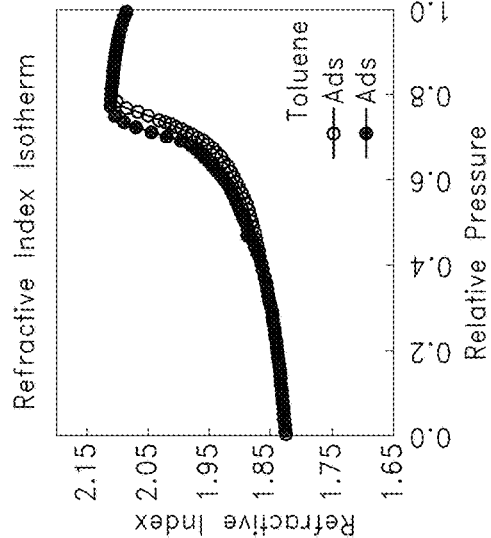
FIGS. 3A-3E are plots depicting adsorption and desorption isotherms of toluene in silicon surfaces obtained at various etching times. The etching times shown are as follows.
Figure 3B:
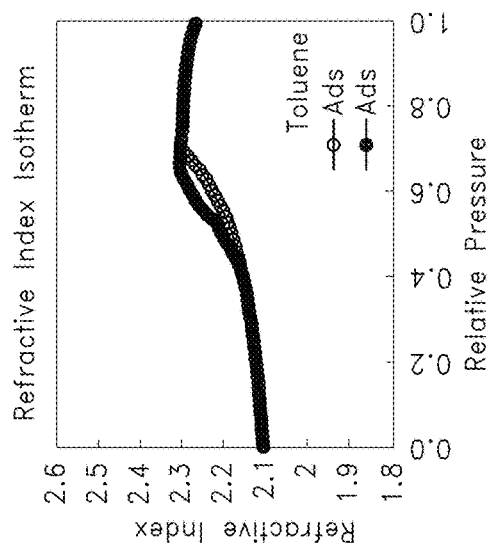
Figure 3C:
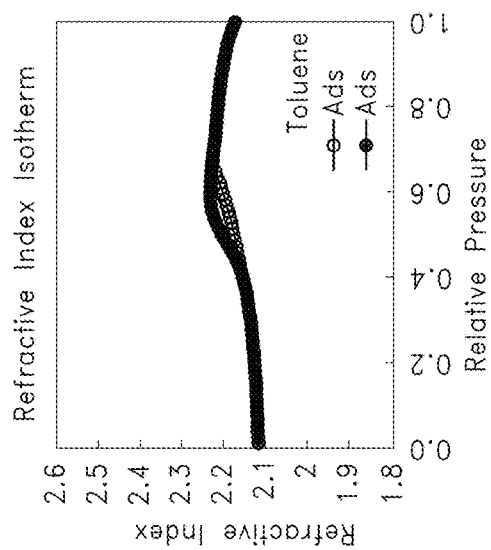
Figure 3D:
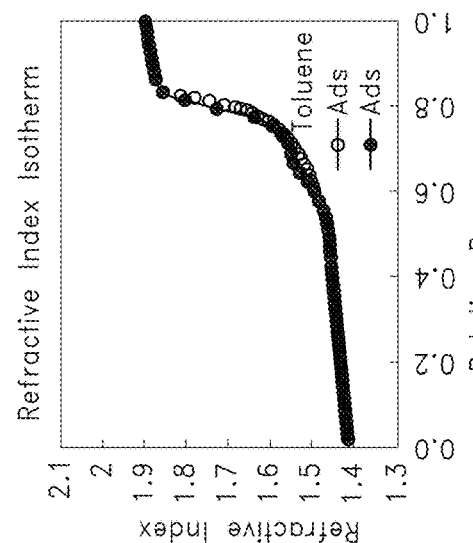
Figure 3E:
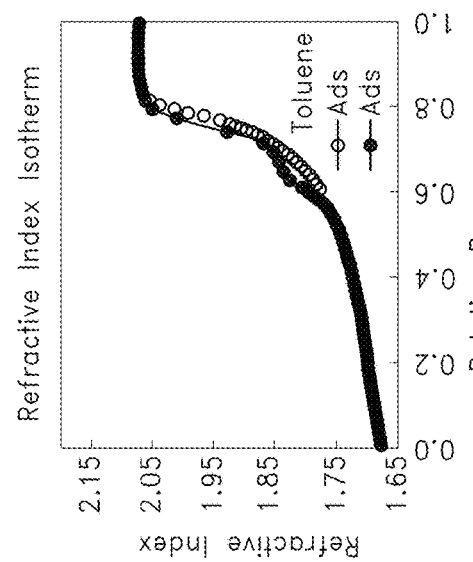

Spectroscopic ellipsometry was applied to characterize physical parameters of these porous substrates, and adsorption and desorption isotherms of toluene in silicon surface were obtained under a broad range of relative pressures (sample pressure/saturated pressure) as shown in FIGS. 3A-3E. FIGS. 3A-3E depicts adsorption and desorption isotherms of toluene in silicon surfaces obtained at variable etching time: FIG. 3A: 2 mins, FIG. 3B: 10 mins, FIG. 3C: 20 mins, FIG. 3D: 30 mins, and FIG. 3E: 40 mins. The results were fitted by the Kelvin equation and Forouhi-Bloomer's model to extract their pore size distribution from these isotherms as shown in FIGS. 4A-4E. See Liu, Y.; Xu, G.; Song, C.; Weng, W.; Du, P.; Han, G. *Thin Solid Films* 2007, 515, 3910-3913, Keita, A. S.; Naciri, A. E.; Delachat, F.; Carrada, M.; Ferblantier, G.; Slaoui, A. *physica status solidi (c)* 2010, 7, 418-422, and Wongmanerod, C.; Zangooie, S.; Arwin, H. *Applied Surface Science* 2001, 172, 117-125, which are incorporated by reference herein in the entirety. FIGS. 4A-4E depicts the pore size distributions of silicon surfaces obtained at variable etching time: FIG. 4A: 2 mins, FIG. 4B: 10 mins, FIG. 4C: 20 mins, FIG. 4D: 30 mins, and FIG. 4E: 40 mins. The calculated porosity, pore size and thickness of porous films are shown in FIG. 1 panel E. The line with diamonds represents pore size and the line with circles represents porosity. The inset in FIG. 1 panel E shows the correlations between surface morphologies of NIMS substrates and etching time. Both pore size and porosity of these substrates linearly increase with etching time, consistent with the observations by SEM. Pore size of these substrates shows a gradual increase from ~4 nm to 12 nm while their porosity increases from ~7% to 70% of the total etched volume. The etching depth of these porous substrates sharply rises from ~250 nm to 2.4 µm, and then fluctuates in the range of 2.2 µm to 2.5 µm.

Example 3

This example illustrates a non-limiting procedure whereby the correlation between molecular weight and porosity in relation to NIMS sensitivity was determined. The example indicates a morphology-dependent NIMS sensitivity behavior.

Analytes Used and NIMs Protocol.

Figure 5:
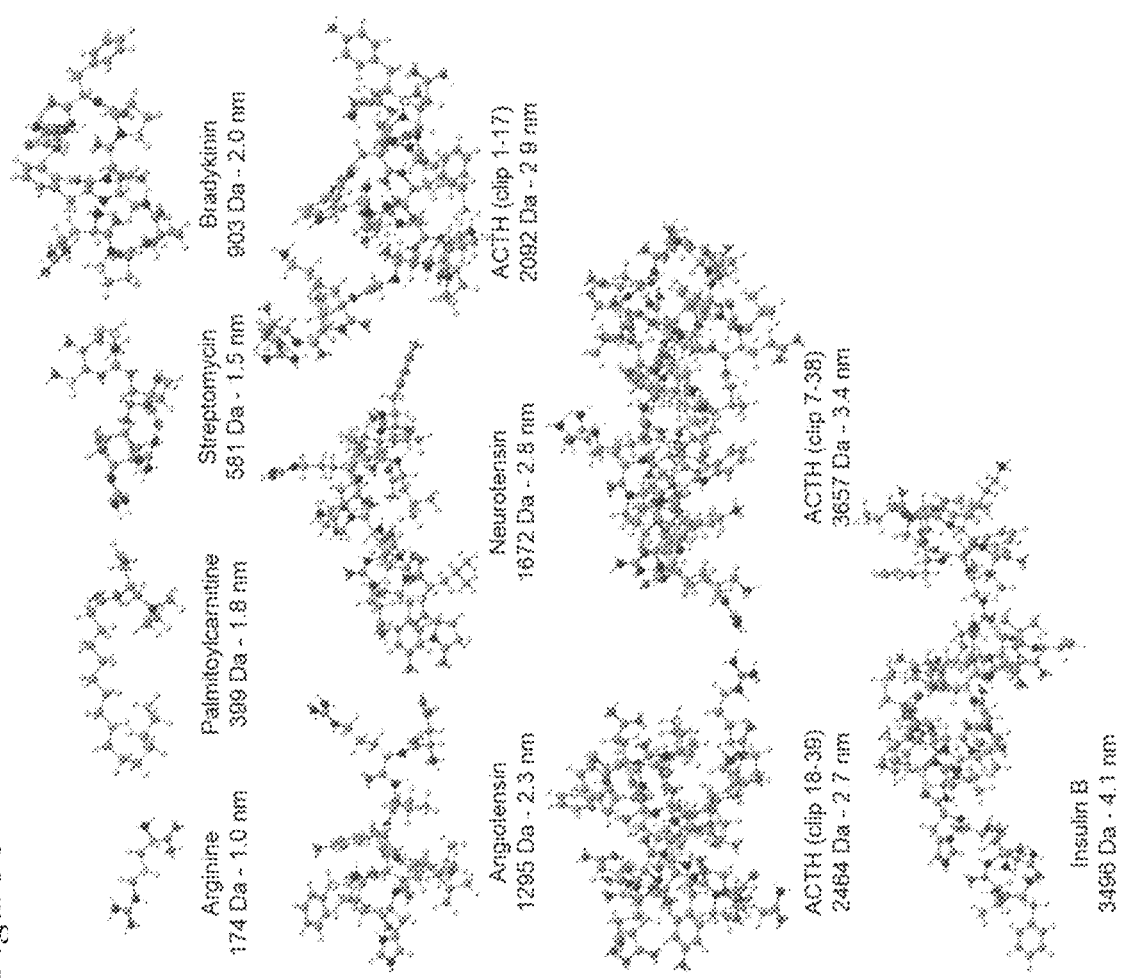
FIG. 5 shows the optimized geometries of the analytes calculated by Chem3D, and their molecular lengths measured from the longest sides.

Nanostructured silicon substrates were coated with BisF17 initiator and further examined as NIMS surfaces using chemically and physically diverse analytes. The analytes ranged from 174-3657 Da and included arginine, palmitylcarnitine, streptomycin, bradykinin, angiotensin, neurotensin, ACTH residues ('clip' 1-17, 18-39, 7-38) and insulin B as shown in FIG. 5. FIG. 5 shows optimized geometries of the analytes calculated by Chem3D, and their molecular lengths measured from the longest sides. Ten nanoliters of each analyte solution was deposited onto the various NIMS surfaces using acoustic printing. This enabled multiple replicates to control spot-to-spot variations over the same NIMS surface. Mass spectrometry imaging was performed for data acquisition and raw data analysis was performed using OpenMSI software. See Rübel, O.; Greiner, A.; Cholia, S.; Louie, K.; Bethel, E. W.; Northen, T. R.; Bowen, B. P. *Analytical Chemistry* 2013, 85, 10354-10361, which is incorporated by reference herein in the entirety.

Effect of Surface Morphology on NIMS Sensitivity.

Figure 6:
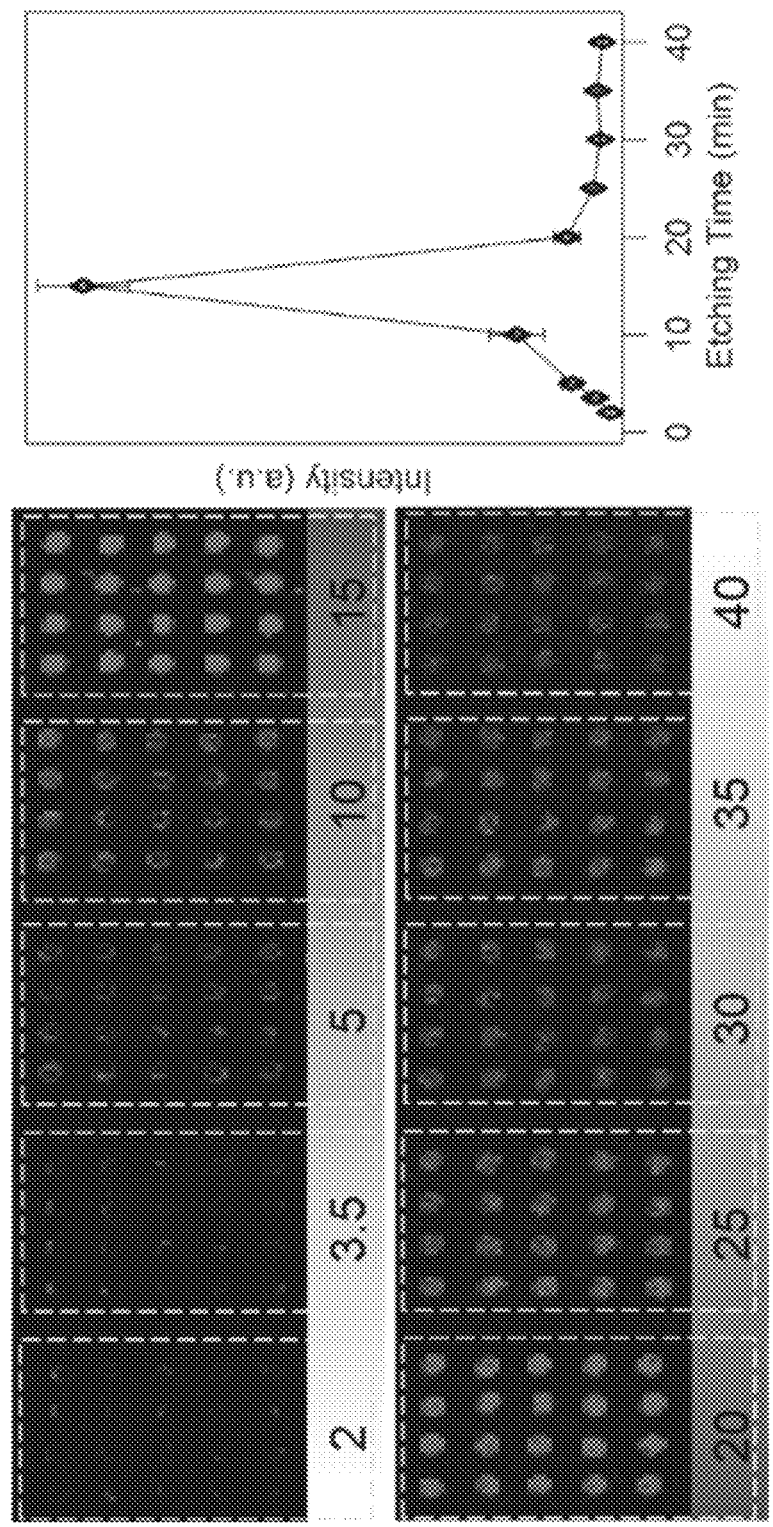
FIG. 6 depicts a NIMS sensitivity comparison of the analyte ACTH (clip 18-39) using silicon substrates obtained at different etching time from 2 mins to 40 mins.

FIG. 6 depicts a NIMS sensitivity comparison of the analyte ACTH (clip 18-39) using silicon substrates obtained at different etching time from 2 mins to 40 mins. It includes 10 sets of 20 replicate sample spots of the analyte ACTH (clip 18-39) printed on 10 different NIMS surfaces with increasing pore size. The average intensity of mass spectra corresponding to ACTH (clip 18-39) are plotted with error bars on the right side of FIG. 6. From this analysis, it is apparent that ACTH (clip 18-39) shows a strong dependency on the NIMS surface morphologies. Its signal intensity gradually increases with the etching time of substrates and reaches a maximum at 15 mins, and afterwards it gradually decreases. This observation indicates the desorption/ionization process of this molecule highly relies on the surface structures of silicon substrates.

Figure 7:
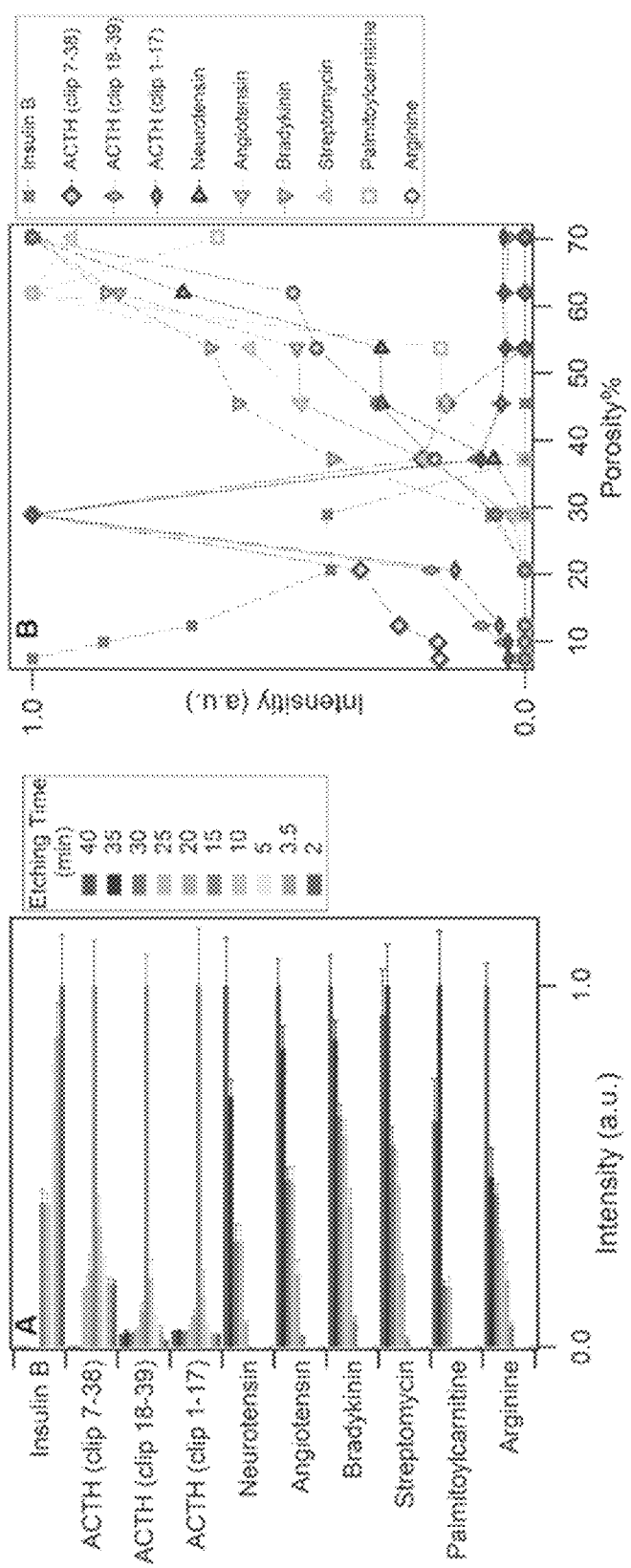
FIG. 7 depicts a NIMS sensitivity study of nanostructured silicon substrates etched at 2 to 40 mins using a variety of molecules (n=20). Panel A shows a histogram of NIMS signals showing their intensity change by the substrates' etching time. Panel B shows a scatter plot of NIMS signals by the substrates' porosity.
Figure 8:
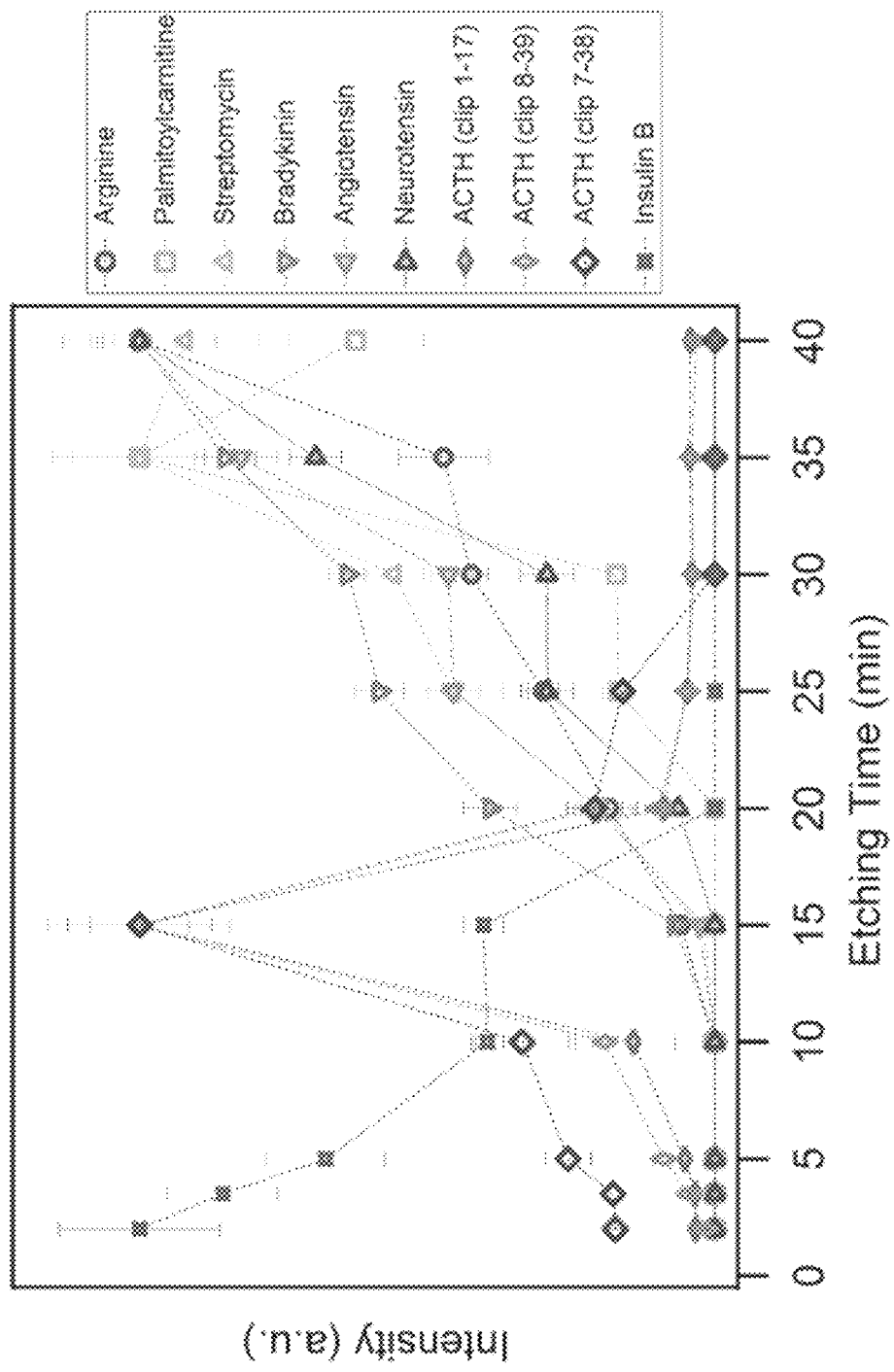
FIG. 8 is a scatter plot of NIMS signal changes with the substrates etching time.

NIMS sensitivity of this series of nanostructured silicon substrates was examined with the complete panel of analyte molecules via imaging mass, as illustrated in FIG. 6 for ACTH (clip 18-39), using 20 sample spots of each analyte acoustically printed onto these substrates. Mass spectra of these sample spots were averaged and their NIMS peak intensities are shown in FIG. 7. FIG. 7 shows the NIMS sensitivity of nanostructured silicon substrates etched at 2 to 40 mins. FIG. 7 Panel A shows a histogram of NIMS signals showing their intensity change by the substrates' etching time and FIG. 8 shows the corresponding scatter plot. FIG. 7 panel B shows a scatter plot of NIMS signals by the substrates' porosity. To determine statistically significant changes in intensity, a single factor ANOVA was performed on the averaged NIMS signals for each analyte from these NIMS substrates, followed by a post-hoc two sample t-test (Table 2, shown below). This analysis showed, not surprisingly, that etching time is a significant factor in determining the signal intensity for all analytes examined.

etching time and are only detectable with the substrates etched at 15 mins or longer with the highest signal at 35 mins and 40 mins.

These results provide evidence of the strong coupling between NIMS surface morphology and desorption/ionization efficiency of analytes. NIMS substrates fabricated at short etching time (<15 mins) have the highest sensitivity for the largest molecules (e.g. insulin B) while the substrates fabricated at long etching time (>15 mins) reveal high performance on ionizing small molecules. The etching time now most widely used for NIMS, 15 mins, is found to represent an intermediate value.

NIMS surfaces were examined herein where the surface nanostructures are coated/filled with initiator. According to FIG. 7, substrates fabricated at long etching time that have

TABLE 2

P-values of different analytes' NIMS signals calculated from single factor ANOVA and a post-hoc two sample t-test (n = 20).

| Source of Variation | | P-value | Source of Variation | | P-value |
|---|---|---|---|---|---|
| Arginine | Between Groups | 1.17E−65 | ACTH (clip 1-17) | Between Groups | 1.22E−133 |
| | 15 min-20 min | 8.15E−11 | | 2 min-3.5 min | 1.43E−01 |
| | 20 min-25 min | 1.23E−10 | | 3.5 min-5 min | 1.30E−08 |
| | 25 min-30 min | 3.22E−17 | | 5 min-10 min | 1.08E−05 |
| | 30 min-35 min | 8.31E−03 | | 10 min-15 min | 3.93E−19 |
| | 35 min-40 min | 8.34E−16 | | 15 min-20 min | 1.61E−16 |
| Palmitoylcarnitine | Between Groups | 1.23E−35 | | 20 min-25 min | 1.51E−14 |
| | 25 min-30 min | 2.71E−01 | | 25 min-30 min | 1.30E−03 |
| | 30 min-35 min | 1.67E−08 | | 30 min-35 min | 1.93E−04 |
| | 35 min-40 min | 5.15E−06 | | 35 min-40 min | 8.67E−02 |
| Streptomycin | Between Groups | 8.31E−72 | ACTH (clip 8-39) | Between Groups | 1.51E−174 |
| | 15 min-20 min | 1.73E−12 | | 2 min-3.5 min | 1.97E−08 |
| | 20 min-25 min | 1.07E−12 | | 3.5 min-5 min | 1.24E−10 |
| | 25 min-30 min | 3.08E−05 | | 5 min-10 min | 8.33E−09 |
| | 30 min-35 min | 5.09E−15 | | 10 min-15 min | 2.78E−27 |
| | 35 min-40 min | 2.18E−02 | | 15 min-20 min | 1.42E−23 |
| Bradykinin | Between Groups | 7.77E−89 | | 20 min-25 min | 2.33E−09 |
| | 15 min-20 min | 5.16E−20 | | 25 min-30 min | 6.87E−09 |
| | 20 min-25 min | 1.79E−16 | | 30 min-35 min | 1.84E−03 |
| | 25 min-30 min | 2.79E−05 | | 35 min-40 min | 1.85E−06 |
| | 30 min-35 min | 1.30E−16 | ACTH (clip 7-38) | Between Groups | 1.24E−87 |
| | 35 min-40 min | 8.02E−08 | | 2 min-3.5 min | 1.78E−01 |
| Angiotensin | Between Groups | 2.00E−95 | | 3.5 min-5 min | 1.22E−08 |
| | 15 min-20 min | 2.14E−14 | | 5 min-10 min | 2.86E−04 |
| | 20 min-25 min | 1.21E−20 | | 10 min-15 min | 2.69E−20 |
| | 25 min-30 min | 2.59E−01 | | 15 min-20 min | 1.37E−19 |
| | 30 min-35 min | 7.00E−20 | | 20 min-25 min | 9.28E−05 |
| | 35 min-40 min | 5.13E−10 | Insulin B | Between Groups | 5.09E−43 |
| Neurotensin | Between Groups | 4.74E−66 | | 2 min-3.5 min | 2.86E−04 |
| | 20 min-25 min | 9.33E−16 | | 3.5 min-5 min | 8.25E−07 |
| | 25 min-30 min | 4.68E−01 | | 5 min-10 min | 2.70E−11 |
| | 30 min-35 min | 3.76E−27 | | 10 min-15 min | 2.56E−01 |
| | 35 min-40 min | 5.68E−10 | | | |

The ACTH peptides are subsets of the same peptide and therefore represent some control of analyte chemistry. Despite their different molecular weights and molecular sizes, they show strikingly similar signal dependence on porosity as well as an optimal signal at 15 min etching corresponding to an average pore size of 7 nm and porosity of 29% (FIG. 7). In contrast, insulin B shows the strongest signal on substrates etched for only 2 min (pore size-4 nm; porosity-7%) and no NIMS signal can be detected with etching times longer than 20 mins. Moving from 2 to 15 min etching time increases ACTH peptide signal 5.8 fold and decreases insulin B signal 2.5 fold. In contrast, analytes with molecular weight smaller than 2000 Da, despite their chemical diversity (arginine palmitoylcarnitine, streptomycin, bradykinin and angiotensin), showed similar signal response to the highest porosity and therefore large surface area have the highest sensitivity for small molecules. This is consistent with the view of a surface energy driven process, where increased surface area results in more efficient desorption/ionization. Without being bound by any particular theory, the surprising behavior of the largest peptides is believed to reflect a strong interaction between initiator coated nanostructures and the analytes that interferes with the desorption/ionization process. In which case, the combination of small pores has decreased adsorption energies and can provide more explosive and directed release of energy required by large analyte molecules during their desorption/ionization.

Figure 9:
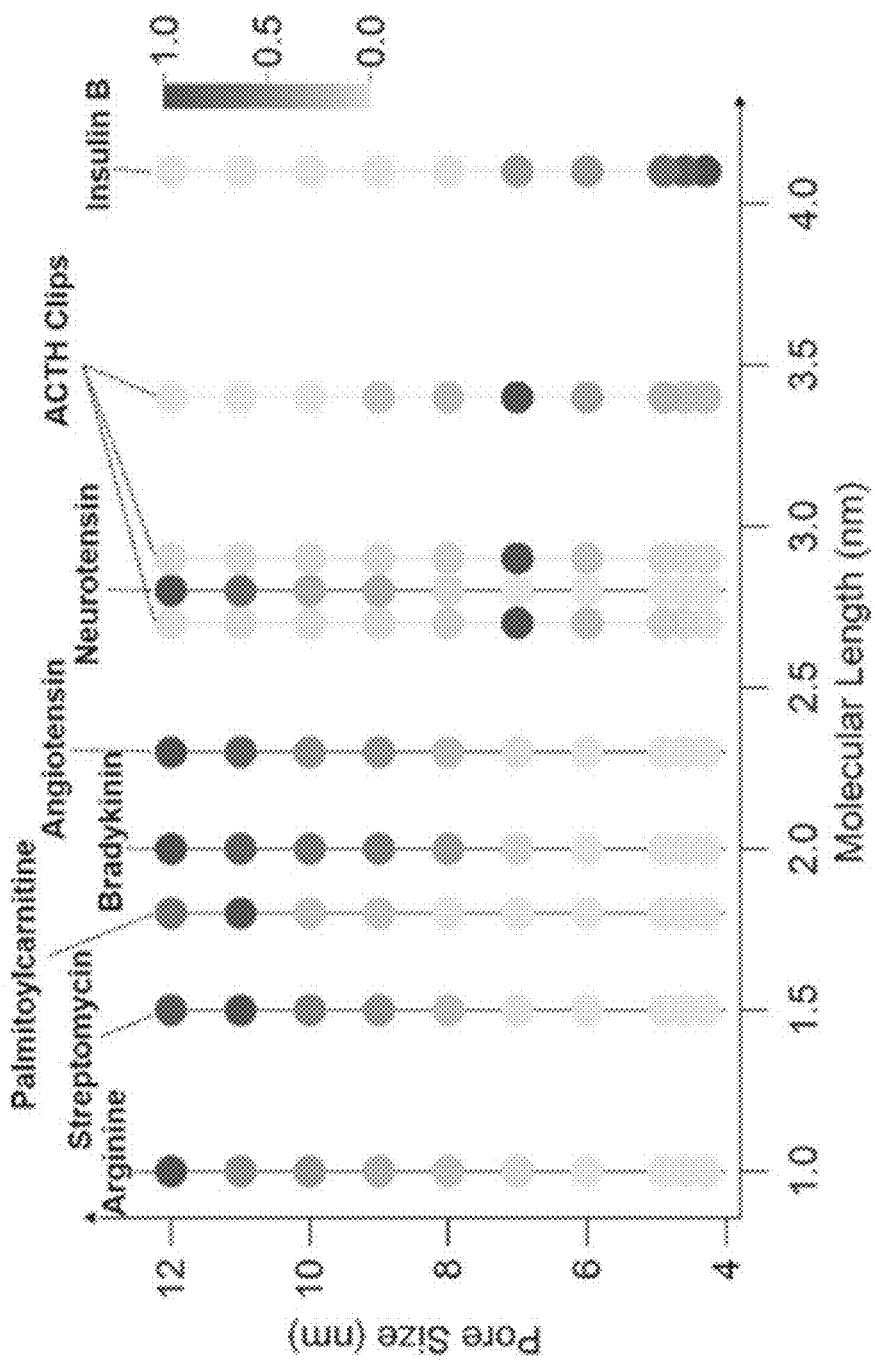
FIG. 9 depicts the correlation of pore sizes and molecular length regarding NMS sensitivity. The signal is normalized to the maximum intensity for each analyte.

To further examine the connection between pore size and analyte size in decreasing the sensitivity for high molecular weight peptides, the molecular spatial conformations were estimated. Optimized Chem3D structures showed the spatial lengths of analytes range from 1 nm to 4 nm (FIG. 5) thus they are on the same scale of the pore sizes of this series of NIMS surfaces (FIG. 9). FIG. 9 shows the correlation of pore sizes and molecular length regarding NIMS sensitivity, as shown, the signal is normalized to the maximum intensity for each analyte. Without being bound by any particular theory, coated porous features on silicon surfaces is thought to turn into physical traps during surface melting process and cage analyte molecules inside NIMS surfaces. Under this mechanism, trapping effect would become more severe when the spatial dimensions of molecules become comparable to the initiator coated pore sizes. The substrates obtained at short etching time have small pores (<7 nm) and low porosity (<25%) allowing large molecules to sit on top of the nanostructures avoiding 'trapping'.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one of skill in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those of skill in the art. The various aspects and embodiments disclosed herein are for purposes of illustration and are not intended to be limiting, with the true scope and spirit being indicated by the following claims.

What is claimed is:

1. A method for making a porous semiconductor substrate for ionizing a target comprising:
   (a) providing a semiconductor material;
   (b) determining a desired length of etching time of the semiconductor material based on the molecular weight of the target, and determining a desired porosity wherein the desired porosity is determined to be no more than 40% if the target is larger than 2000 Daltons in molecular weight;
   (c) etching the semiconductor material for the desired length of etching time to produce an etched semiconductor material; and
   (d) contacting the etched semiconductor material with an initiator to produce the porous semiconductor substrate.

2. The method of claim 1, wherein in step (b) the desired length of etching time is determined to be no more than 20 minutes if the target is larger than 2000 Daltons in molecular weight.

3. The method of claim 1, wherein in step (b), the desired length of etching time is determined to be at least 15 minutes if the target is no more than 2000 Daltons in molecular weight.

4. The method of claim 1, wherein in step (b) the desired porosity is determined to be at least 35% if the target is no more than 2000 Daltons in molecular weight.

5. The method of claim 1, wherein in step (b) the desired average pore size is determined to be no more than 10 nm if the target is larger than 2000 Daltons in molecular weight.

6. The method of claim 1, wherein in step (b) the desired average pore size is determined to be at least 8 nm if the target is no more than 2000 Daltons in molecular weight.

7. The method of claim 1, wherein in step (c) the semiconductor material is etched using hydrofluoric acid electrochemical etching method or inductively coupled plasma reactive ion etching method.

8. The method of claim 1, wherein the semiconductor material comprises a material selected from the group consisting of Group IV semiconductors, Group I-VII semiconductors, Group II-VI semiconductors, Group III-V semiconductors, sphaelerite structure semiconductors, Wurtzite Structure Compounds, I-II-VI2 semiconductors, silicon, and a combination thereof.

9. The method of claim 1, wherein the initiator is selected from the group consisting of lauric acid, polysiloxanes, chlorosilanes, methoxy silanes, ethyoxy silanes, fluorous siloxanes and fluorous silanes.

10. The method of claim 1, wherein the target is selected from the group consisting of lipids, amino acids, small molecules, peptides, drugs, proteins, and any combination thereof.

11. A method for ionizing a target, comprising:
    providing a porous semiconductor substrate having a desired porosity, a desired average pore size, or both, wherein the desired porosity, the desired average pore size, or both are determined based on the molecular weight of the target, and wherein the desired porosity is determined to be no more than 40% if the target is larger than 2000 Daltons in molecular weight;
    delivering the target to the semiconductor substrate to form a target-loaded substrate; and
    irradiating the target-loaded substrate.

12. The method of claim 11, further comprising
    (i) providing a semiconductor material;
    (ii) determining a desired length of etching time of the semiconductor material based on the molecular weight of the target, the desired porosity of the porous semiconductor substrate, the desired average pore size of the porous semiconductor substrate, or a combination thereof;
    (iii) etching the semiconductor material to produce an etched semiconductor material; and
    (iv) contacting the etched semiconductor material with an initiator to produce the porous semiconductor substrate having the desired porosity, the desired average pore size, or both.

13. The method of claim 11, wherein the desired average pore size is no more than 10 nm if the target is larger than 2000 Daltons in molecular weight.

14. The method of claim 11, wherein the desired average pore size is at least 8 nm if the target is no more than 2000 Daltons in molecular weight.

15. The method of claim 12, wherein the semiconductor material comprises a material selected from the group consisting of Group IV semiconductors, Group I-VII semiconductors, Group II-VI semiconductors, Group III-V semiconductors, sphaelerite structure semiconductors, Wurtzite Structure Compounds, I-II-VI2 semiconductors, silicon, and a combination thereof.

16. The method of claim 12, wherein the target is a constituent of a sample selected from a biological sample, an environmental sample, a clinical sample, a forensic sample, or a combination thereof.

* * * * *